United States Patent [19]

Weise et al.

[11] Patent Number: 5,424,836
[45] Date of Patent: Jun. 13, 1995

[54] APPARATUS FOR CONTACT-FREE OPTICAL MEASUREMENT OF A THREE-DIMENSIONAL OBJECT

[75] Inventors: Thomas Weise; Rudger Rubbert, both of Berlin, Germany

[73] Assignee: Geyer Medizin- und Fertigungstechnik GmbH, Germany

[21] Appl. No.: 70,264

[22] Filed: Jun. 2, 1993

[30] Foreign Application Priority Data

Jun. 3, 1992 [DE] Germany .................. 42 18 219.0

[51] Int. Cl.⁶ .................. G01B 11/24; G01N 21/86
[52] U.S. Cl. .................. 356/376; 356/241; 250/561
[58] Field of Search .................. 356/241, 376, 375; 250/561, 562, 563

[56] References Cited

U.S. PATENT DOCUMENTS

| | | | |
|---|---|---|---|
| 4,500,206 | 2/1985 | Cole et al. | 356/376 |
| 4,668,192 | 5/1987 | Lavin | 433/205 |
| 4,900,144 | 2/1990 | Kobayashi | 356/376 |
| 5,004,929 | 4/1991 | Kakinoki et al. | 250/561 |
| 5,111,056 | 5/1992 | Yoshimura et al. | 356/376 |

FOREIGN PATENT DOCUMENTS

| | | | |
|---|---|---|---|
| 0391532 | 10/1990 | European Pat. Off. | 356/376 |
| 3829925 | 3/1990 | Germany | 356/376 |
| 60-55211 | 3/1985 | Japan | 356/376 |
| WO9105520 | 5/1991 | WIPO | 356/376 |

*Primary Examiner*—Rolf Hille
*Assistant Examiner*—Minhloan Tran
*Attorney, Agent, or Firm*—Paul & Paul

[57] ABSTRACT

A description is given of an apparatus for the contact-free, spatial measurement of a poorly accessible, three-dimensional object (9) optically by taking surface photographs, having an optic ray source, a recording unit (10, 11) for recording optic rays (15, 18, 19, 25), and an evaluation unit for the evaluation of the data transmitted by the optic rays. In order to make it possible for objects to be measured accurately, preferably in space, in contact-free manner in confined spaces, and for the measuring data results to be recorded, the invention provides that a carrier (4) is movable on at least one guide device (2) relative to the object (9) on a guide track (3) towards the frame (1), that the carrier (4) is able to travel on the guide device (2) by means of a motor (7), that a deflector device (12, 13, 13') is fixed to the carrier (4) in such a way that at least one ray (18, 19, 25; 18', 19', 25') reflected by the object is deflected towards the recording unit (10, 11), that the position and orientation of the frame (1) relative to the object (9) is clearly defined at any time, that the position and orientation of the carrier (4) relative to the frame (1) is clearly defined at any time, that the evaluation unit (11a) has devices for storing data relating to the rays (18', 19', 25') reflected by the object (9) in the form of image elements, -lines, and/or image planes, and that the evaluation unit (11a) has devices for the processing of image data stored.

21 Claims, 13 Drawing Sheets

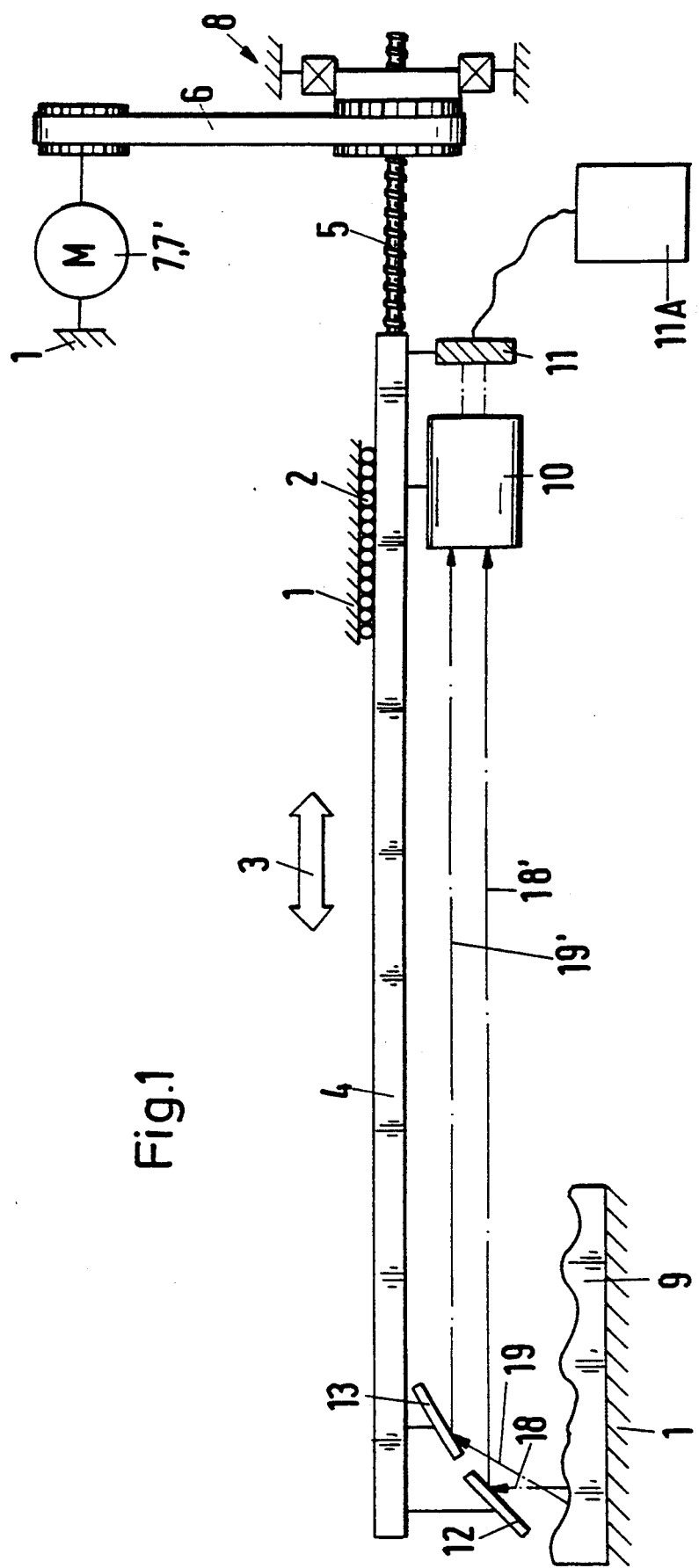

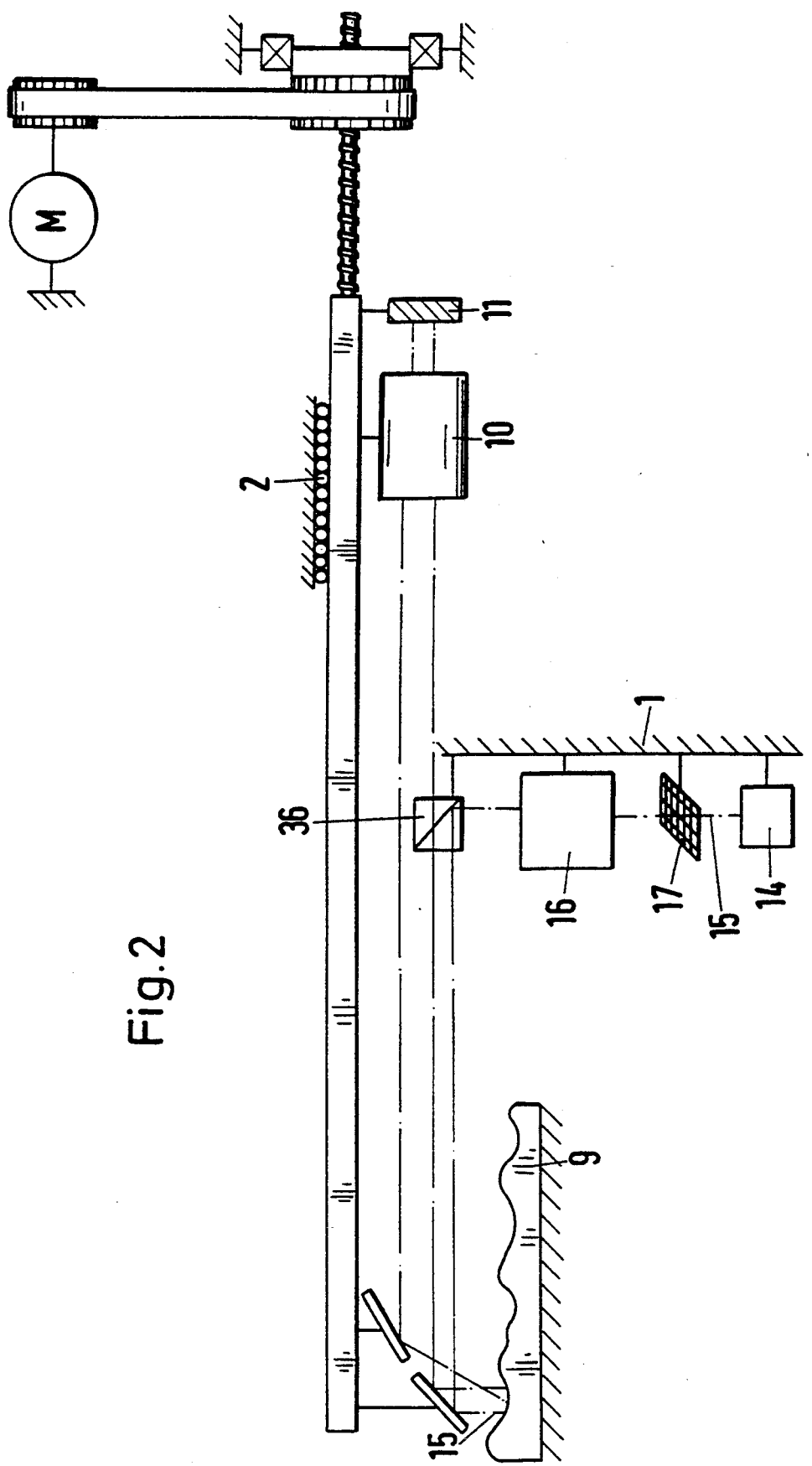

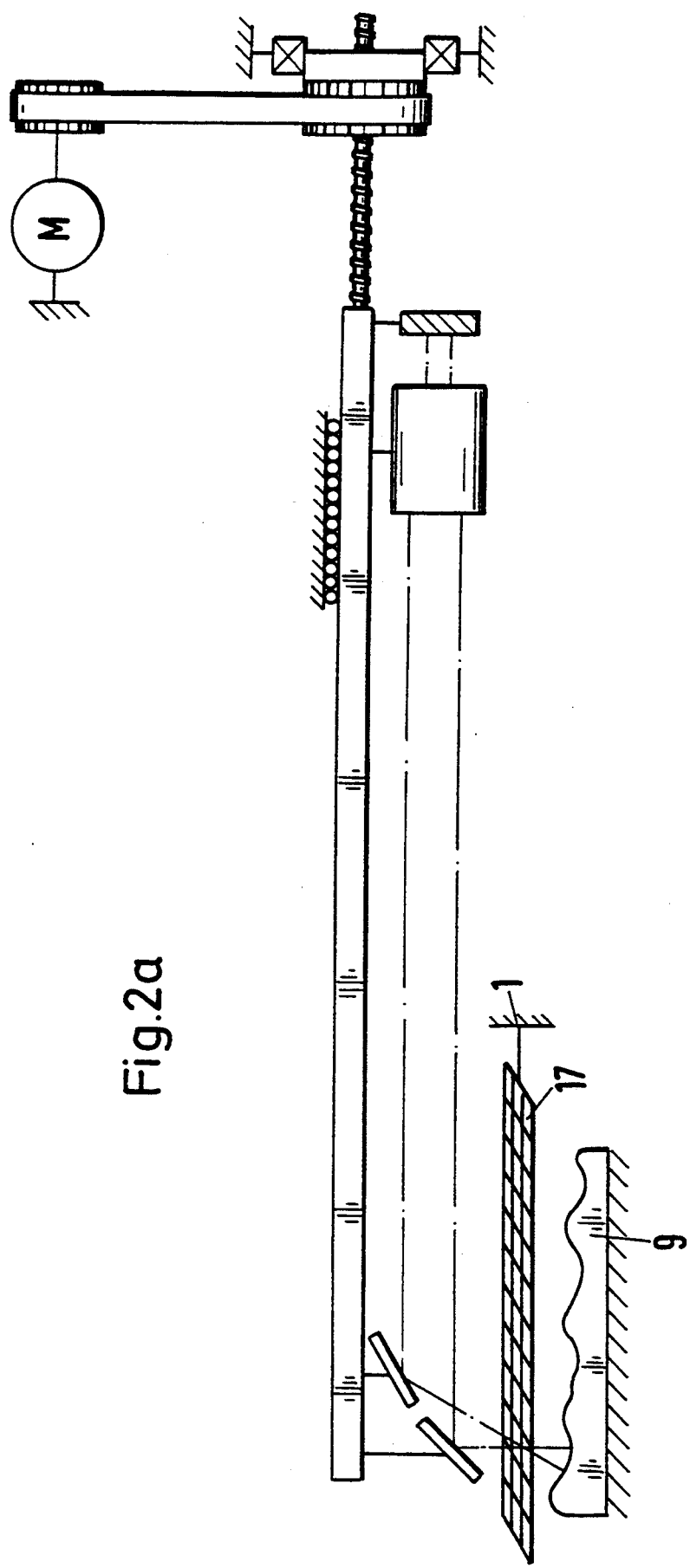

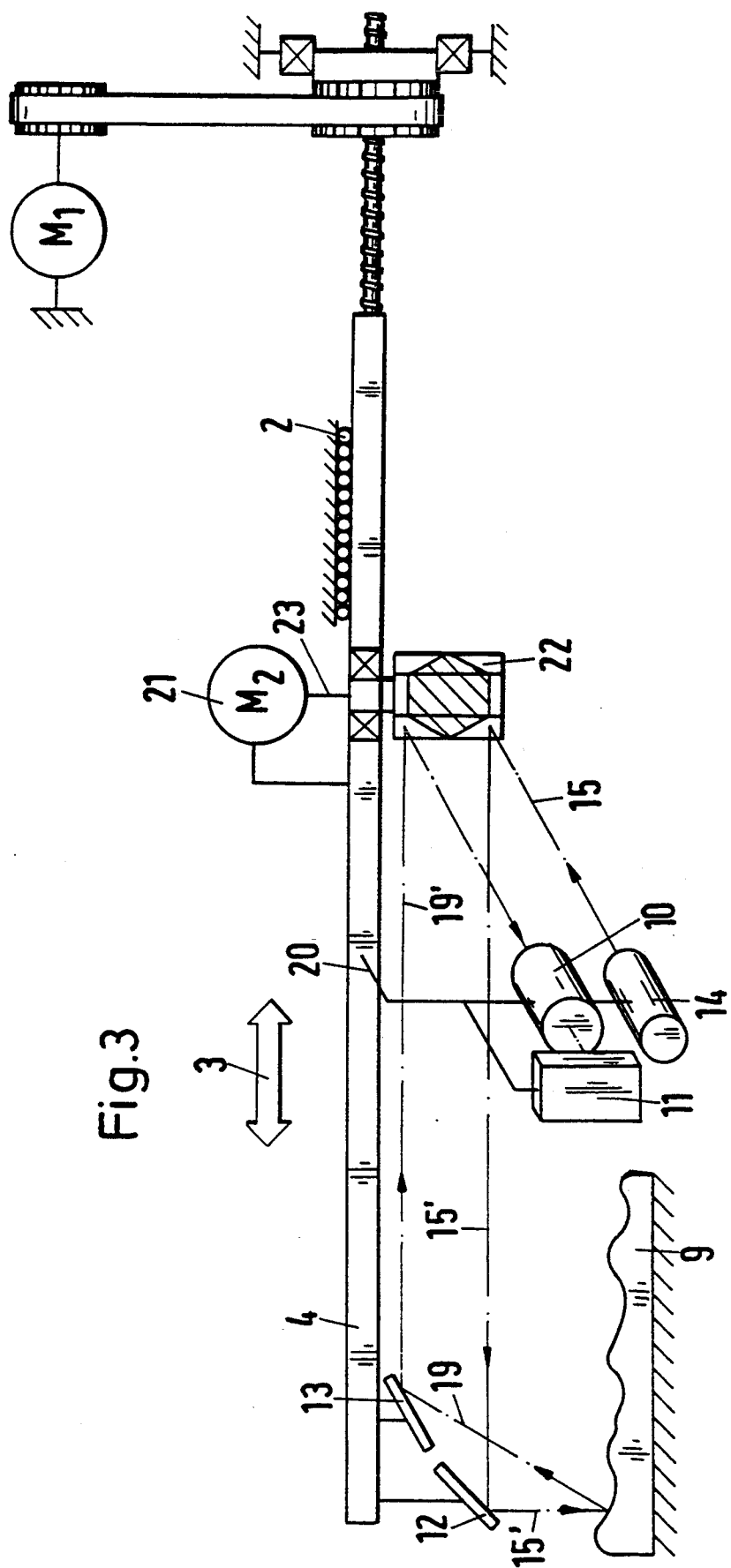

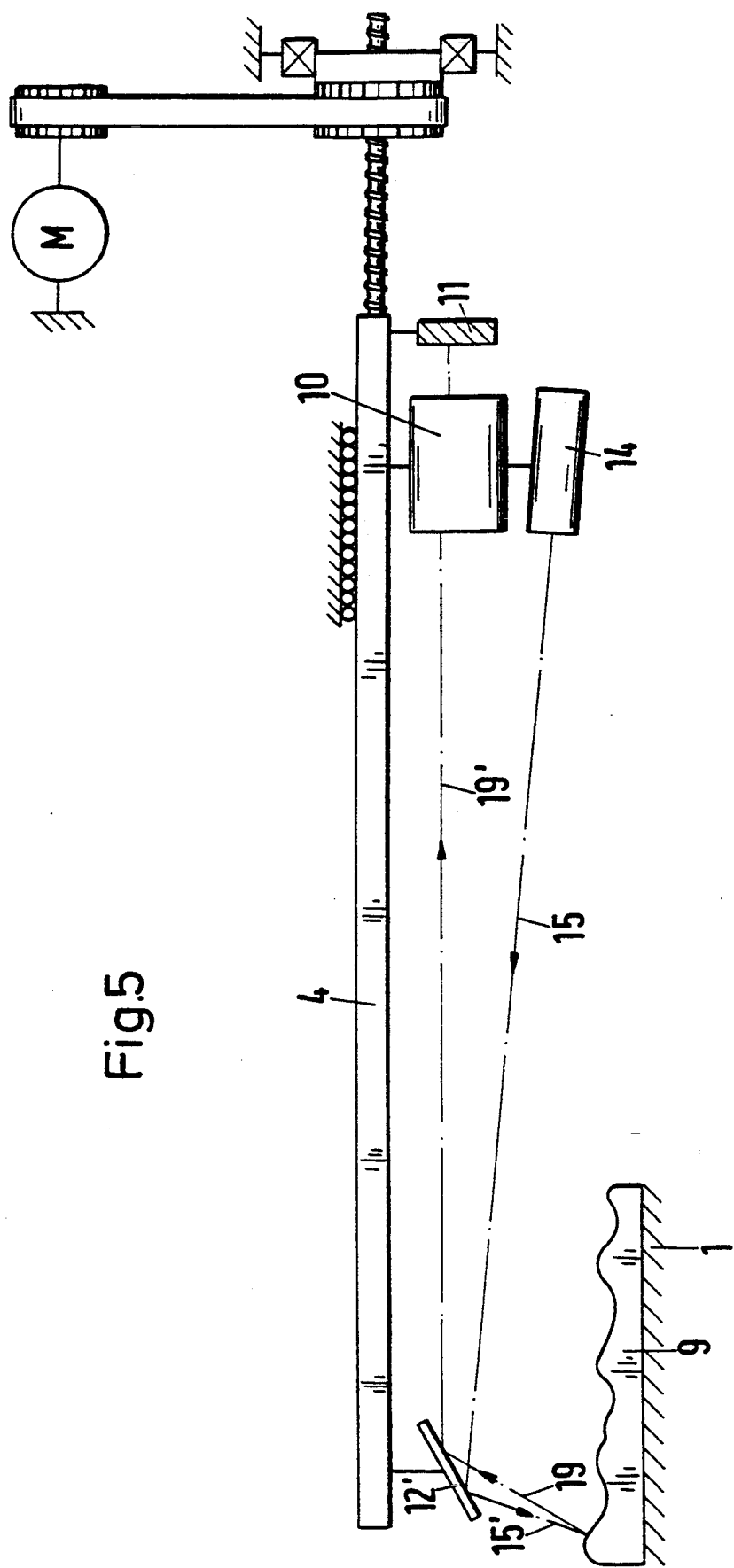

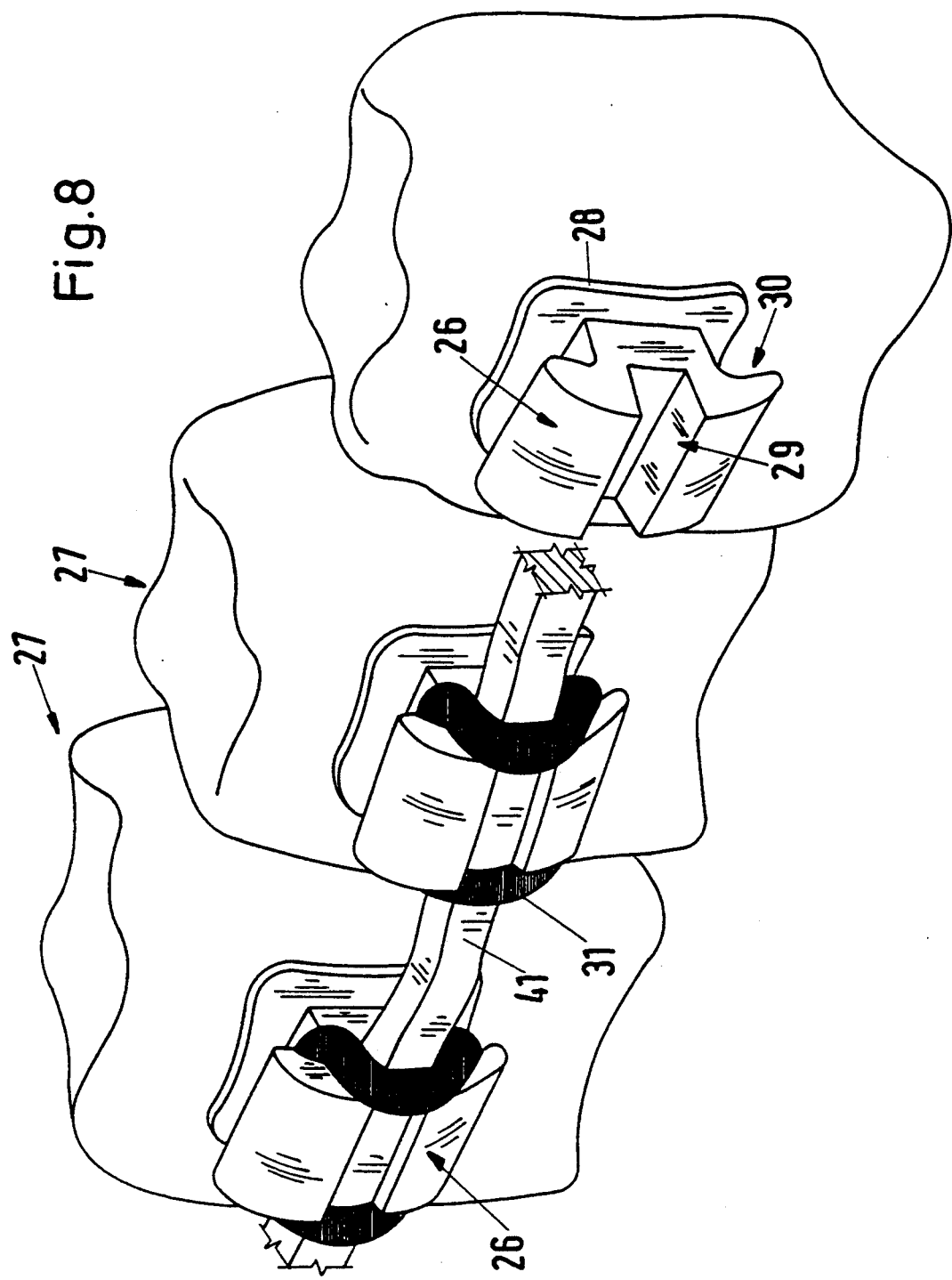

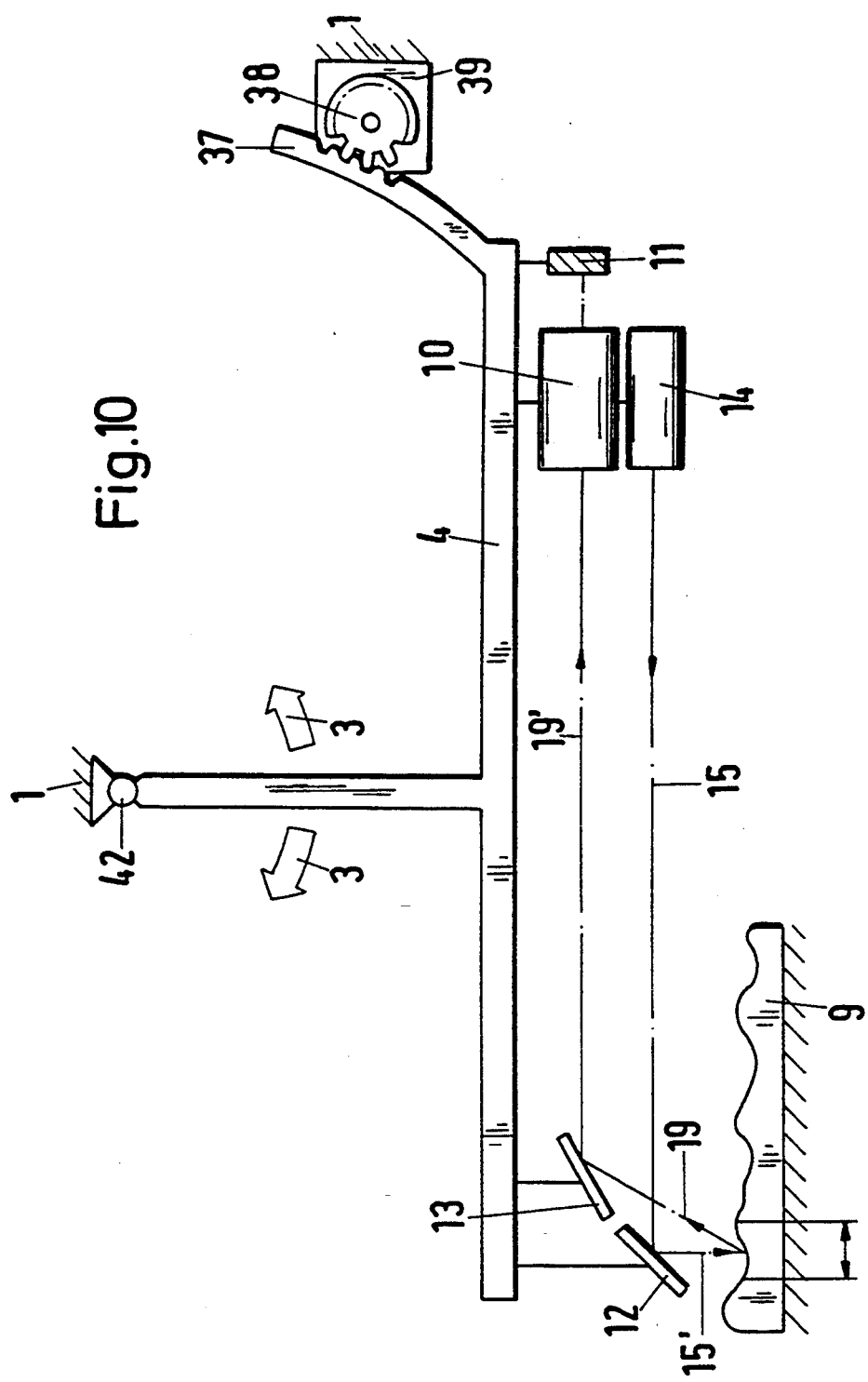

APPARATUS FOR CONTACT-FREE OPTICAL MEASUREMENT OF A THREE-DIMENSIONAL OBJECT

FIELD OF THE INVENTION

The invention relates to an apparatus for the contact-free measurement of a poorly accessible, three-dimensional object, optically, by taking surface photographs, having an optic ray source, a recording unit for recording optic rays and an evaluation unit for the evaluation of data transmitted by the optic rays.

BACKGROUND OF THE INVENTION

A method is known of measuring objects mechanically in the conventional way and also of measuring them optically, e.g. by taking 3-D photographs. With this method, in order to spatially determine the object, the light section method and the stereo recording method are known, amongst others. Measurements taken using optic apparatus of this kind is problematic because the object to be measured must be sufficiently optically accessible, i.e. the surfaces which are to be measured must be directly visible.

However, a number of instances arise where access to the object to be measured is so poor that direct visibility of the object, at least from the angle of view required for the measurement to be taken, is not possible. This is most frequently the case due to the spatial limitations for the measuring apparatus, and so in other words the space around the object to be measured is so small that neither the measuring apparatus nor a sufficiently large optical instrument with deflector mirrors and the like for taking the measurements is able to be placed in position or accommodated.

Such an example is in dentistry where a set of teeth has to be measured for jaw-orthopaedic purposes, e.g. if gaps between teeth have to be corrected by the use of the "Edge-Wise-Wire Spring-Technique". With this technique, clamping elements (known as brackets) are fixed to the teeth to which elements a wire spring is fixed. This is shaped in such a way that it applies the necessary forces and moments to the teeth for correction in the necessary way. To adjust the correct forces and moments, the wire spring has to be correctly set, and a specially made wire spring has to be made for each individual patient when that patient is treated. In this respect, a proposal has already been made to use computer controlled bending machines to produce the correctly shaped wire springs. To this end, at least the spatial coordinates of the bracket must be accurately known. Also, it would be helpful if the person treating the patient were to have exact data relating to the chewing surfaces, for the aim of correcting the teeth is to produce positioning of the teeth where the chewing surfaces of the corresponding teeth of the upper and lower jaw are correct relative to each other.

SUMMARY OF THE INVENTION

The aim of the invention is therefore to create a measuring apparatus of the kind mentioned in the introduction which permits the accurate spatial measurements of objects in contact-free manner in confined spaces and for the measurement result data to be recorded.

This problem is solved according to the invention in that a) a carrier is movable on at least one guide device relative to the object on a guide track opposite the frame;
b) the carrier on the guide device(s) is able to travel by means of at least one actuator,
c) at least one deflector device is fixed to the carrier in such a way that an optic ray reflected by the object is deflected towards the recording unit;
d) the position and orientation of the frame relative to the object is clearly defined at every relevant moment during the recording operation;
e) the position and orientation of the carrier relative to the frame is clearly defined at every relevant moment during the recording operation;
f) the evaluation unit has devices for storing data relating to the rays reflected by the object in the form of image elements and/or image lines and/or image planes; and
g) the evaluation unit has devices for processing the stored image data.

A small space is nearly always present next t$^o$ the object to be measured, at a spacing from the surfaces of the object, this space being visible from the outside through an opening. If a deflector device is provided in this space for rays which are reflected on the object, then it is possible for these rays to be deflected towards a recording unit and to be held there. Hitherto, the problem has existed whereby it has not been possible to completely project and/or cover the object in one single mirror, and this has meant that not even special optical methods have been used for spatial measurements to be taken. This problem is overcome by the invention in that a carrier is used which is movable relative to the object and on which a deflector device is fixed which deflects the rays towards a recording unit where the data is stored and can be evaluated to produce the required spatial data. With this method, however, it is also necessary for the place of the deflector device to be exactly known in relation to the object at every moment during the measuring operation and in every position of the carrier. To this end, it is possible to use per se known measuring instruments or to solve the task constructively.

The movable carrier is guided with precision according to the invention, and it carriers a fixedly adjusted or adjustable deflector device. The apparatus can be used to carry out different measuring methods, wherein the ray source is usually a light source for visible light, and in a special case, to be described hereinafter, it is even possible to use a ray source which illuminates the object generally from the outside.

The invention is based on the idea that owing to the spatial conditions next to the object the deflector device may only be able to contain, and may only contain, a part of the object to be measured, and travels by the movement of the carrier, in single steps or continuously, over the surface of the object to be measured in such a way that a plurality of partial regions is scanned and measured, resulting in partial data or partial images which can then easily be put together, and from which it is possible to build up a spatial picture of the object, if necessary. When this is done, care must be taken to ensure that the position of the guide device relative to the object to be measured is always known. It is possible to provide a rigid coupling or a fixed connection. However, the coupling can also be in the form of a positive juxtaposition or direct connection. It is simply the location of the carrier over its guide unit relative to the object which is to be measurable or known.

The evaluation unit, together with the features according to the invention, is in a position to store the data or partial images completely and to use the capacity of the deflector device to define the:location of the object (using the afore-mentioned measuring devices) to subsequently evaluate the data or partial images. It is also possible to make an initial evaluation of the information or data directly as it has been recorded in order to reduce the amount of data for storage.

By virtue of the defined movement of the deflector device over an object which is to be measured it is advantageously not necessary to measure the entire length which is to be measured of the object as a whole, since the carrier is able to travel over the length of the object and take successive measurements of the partial regions. The same is applicable with respect to the width to be measured, the whole of which does not have to be calculated in one single measurement. Instead, smaller segments of the object can be recorded here which are then put together to form an overall picture when an overall picture is required.

Depending on the application, it is possible to arrange the recording unit(s) and/or the ray source(s), if these latter is/are needed to produce directed rays, so that they are immovable, thus not so that they travel on the carrier. This variant is clearly encompassed by the invention, despite the fact that the description of preferred embodiments is based on an instance of application where the recording unit and ray source travel together.

Since the apparatus according to the invention is designed for measuring the surface of the object (i.e. for two-dimensional measuring), even with so-called 3D-measuring where two (or more) surface photographs have to be taken, which can be evaluated together, it is possible to proceed with the surface measurement alone of a poorly accessible object.

The position and orientation of the frame can be clearly defined relative to the object
by a rigid coupling between the object and frame, or
by avoiding relative movements between the object and the frame, or
by knowing the movements of the object relative to the frame, or
by measuring devices for defining the position and direction of the frame relative to the object.

The position and orientation of the carrier with respect to the frame is defined
by clearly controlling the actuator(s), or
by measuring devices for accurately defining the position and orientation of the carrier with respect to the frame. These kinds of measuring devices may have a measuring system, for example, which is integrated into a servomotor, wherein the actuator can be a motor, e.g. a rotary or linear, electric, pneumatic, hydraulic motor, e.g. a linear stepped motor.

If the stored image data is processed by the evaluation unit, the data relating to the position and orientation of the deflector device over the passage of time is assessed relative to the object. This position is formed on the basis of position and orientation data for the frame in relation to the object and of the position and orientation of the carrier in relation to the frame. In this respect, data relating to the surface photograph of the, at least one, image of the object is prepared which results from the optic rays reflected by the object when the deflector unit moves relative to the object.

Linear or rotary sensors can be used for the measuring devices for defining the position of the carrier and of the moved (oscillating or rotating) mirrors, if their position is known by a control path. According to the invention it is also expedient if the guide track is a straight linear guide, prevented from rotating, and if the carrier is designed as a linear carriage. This gives particularly simple driving and measuring conditions. As an alternative, and according to the invention, it is, however, also possible to design the guide track so that it is circular, and to design the carrier as a hinged door.

One particular embodiment produces a light spot by the use of the directed beam: this is an instance of light spot projection; another method correspondingly produces a line: this is the light section method; and another embodiment produces surface images: this is the stereo-recording-method.

In the case of light spot projection it is advantageous if the optic ray is pivotable in oscillating manner in at least one plane for the purpose of scanning the spot. For this it is necessary to use a ray source which can emit directed optic rays. This ray source, like the recording unit, is preferably fixed to the carrier at a spacing from the deflector device. However, it is also possible to arrange the ray source and also the recording unit in a stationary position outside the carrier. The optic ray will usually be a light ray, and the ray source will usually be a light source. According to the invention, it is designed such that a straight ray is produced by means of which a light spot is copied on the object. By using a camera on the recording unit which is disposed at a specific distance away from the ray source, this spot is measured on the image plane. Since it is able to pivot, the ray can scan the surface of the object line by line, for it oscillates in line direction, for example. If movement of the carrier is step-wise, then the first scanning operation takes place in the first line, and the next scanning operation takes place in the next line, since the carrier advances by one line, and so on and so forth until all lines have been passed through, so that even gap-wise spots are produced. By way of this light spot projection it is thus possible to use the apparatus according to the invention for the purpose of processing surfaces of objects which have been scanned line by line and column by column for the purpose of calculating the spatial coordinates of the illuminated spot of the object. Therein, it is important to determine and evaluate the following:

1. the known angle of the projecting optic ray towards the camera,
2. the distance between the ray source and camera, and
3. the angle, measured by evaluation of the photograph taken, between the projected spot and the ray source.

In this way, it is possible to scan the entire surface of the object to be measured by the ray in line by line and column by column fashion.

Another advantageous embodiment of the invention provides for at least one other deflector unit to be provided for the purpose of oscillatingly deflecting the optic ray which is reflected by the object into another spatial direction and for projecting same into the recording unit. It is thus possible, by using one spot recording unit for each position and orientation of the first deflector unit, to record image data line by line. This linear recording unit allows surface image data to be received for each position and orientation of the first deflector unit.

It is also advantageous according to the invention if a revolving mirror is provided for the purpose of deflecting the optic ray reflected by the object and if the revolving mirror is fixed to the carrier in such a way that the axis of rotation of the revolving mirror is orthogonal (perpendicular) to the direction of movement of the carrier. The mirrors can be used to project an optic ray of very low divergency and small diameter onto the object, and if a revolving mirror is interposed, which preferably has a plurality of mirror planes arranged at angles to one another, then it is possible to arrange these mirror surfaces in such a way that the optic ray passes over the entire width of the object to be measured. Therein, it is expedient if the revolving mirror is driven by means of a step motor or a servomotor in such a way that the current angular position of the revolving mirror is present in the form of measured data. Therefore, the line position of the scanning operation of the surface of the object is also known.

It is also possible to use other drives for the revolving mirrors if only the angular position is known which can be determined functionally with a pawl drive or by way of a suitable sensor, e.g. a rotor.

As an alternative, the rotary movement of the revolving mirror can also be produced by mechanical coupling with the movement of the carrier. A coupling of this kind can be realised by an immovable toothed rod arranged on the carrier guide, into which rod a toothed wheel mounted in the carrier engages which drives the revolving mirror by way of a gear system.

CCD-surface-chips or CCD-line-chips can also be used as a recording units. Instead of using a revolving mirror, as mentioned hereinabove, it is also possible, with another embodiment, to operate with a surface chip, wherein it is then no longer necessary to know the angular position of the revolving mirror since this is only used for lateral deflection of the illuminating ray and this deflection can be seen on the chip.

As an alternative to the afore-described revolving mirror it is also possible to use an oscillating mirror.

For the spatial measurement of three-dimensional measurement it is particularly expedient according to the invention if a) at least one deflector device is provided for at least two rays reflected by the object at an angle relative to each other,
b) at least one recording unit is provided which transmits the data from the, at least two, separate rays to the evaluation unit, and
c) the evaluation unit has devices for forming 3D-data from at least two surface photographs.

If only one recording unit is present, it may be possible for the deflector device to be pivotable so that the rays which are reflected by the object at an angle to each other are deflected over the passage of time in succession towards the recording unit.

According to the invention it can also be very advantageous, if only one recording unit is present, for it to be movably adjustable in height and/or angularly. It is then possible for the device to be brought into the correct position so that the ray which is desired and which is projected by the deflector device can be photographed. 3D-data can be obtained in two ways: by taking a second plan view at a different angle. The two plan views resulting can be produced both simultaneously and successively (or intermittently).

In the case of non-simultaneous recording, the deflector optical instrument can be pivoted after the first measurement journey, for example, through the necessary angle, so that only one mirror surface is necessary. As an alternative, it is possible to use the deflector device with two mirrors, and to move the recording unit in height. One recording unit with one line chip is sufficient in this case.

With another embodiment it is possible to pivot the one recording unit in such a way that the rays fall on the mirror at different angles, or so that the illuminating ray is reflected at a different angle from the ray which is reflected by the surface. Only one mirror surface is then needed. This will be explained hereinafter in conjunction with FIG. 5.

With another embodiment., it is possible to provide the deflector unit with four plane mirrors, and to use one line camera which can be moved in four different positions of height.

For the light section method, a ray of light can be provided which extends in a plane, and which, after being linearly reflected on the object, is directed by way of at least one plane mirror fixed to the carrier into the recording unit which has a surface camera. This avoids the oscillating pivoting movement of the optic ray and thus "starting" of the line by the ray. By virtue of the ray extending in the plane of the line, from the viewpoint of the ray source a thin, straight line can be projected onto the object. When the location of the camera, preferably a surface camera, is disposed outside the plane of extent of the ray, the spatial coordinates can be defined for each of the spots illuminated by the line—thus for an entire line—in the same way as described hereinabove for the light spot projection method.

When the light section method is used and the apparatus with the spread optic ray, preferably a light ray, all spots can be measured which are optically accessible to the relevant ray paths. Thus, a large amount of data is available for evaluation.

With the light section method, a straight line is projected onto the surface of the object, this line appearing to be curved to varying extents when viewed from the recording unit (depending on the height differences of the surface). Accordingly, with the spot projection method, the extent of deflection of the spot when viewed from the recording unit varies.

When a single deflector unit is used (i.e. not, separate travelling capacity) for directed illumination and recording, the mirror surface for the receiving rays is advantageously selected so that it great enough (high enough) for the deflection produced of the line or spot to be completely visible.

If, due to the difference in heights of the surface to be measured, this deflection is very great, and therefore if the height of the deflecting mirror is too great, it is possible to design the two deflector units so that they are able to travel separately for directed illumination and recording. When this happens, the deflector unit for illumination would travel in special small step movements, and whenever that unit is in a new position, the deflector unit would travel through one such path for recording purposes (once again in single steps), so that the whole of the surface required is covered. On the one hand, the recording unit is able to be designed as a line camera, and on the other hand, the height of the recording mirror can be reduced.

According to the invention it is advantageous if a device is provided for designing the optic rays which are directed from the, at least one, ray source, towards the object, for the production of additional data during evaluation of the photographs. This means that the rays can contain a dot-like and/or linear and/or a design corresponding to any pattern.

Expediently, according to the invention, another deflector unit is also provided for deflecting the optic ray in at least one plane.

Usually, it is possible for the directed illumination and for the recording unit to individually use a moving deflector device (which is rotating, movable in translatory fashion, or freely kinematic) to extend or scan the ray path with the passage of time in step-wise manner or Continuously about another spatial coordinate (dimension). It is thus possible, for example, to use an oscillating mirror with a spot ray source to scan a line or accordingly to use a recording unit to record a line for just one spot (e.g. a photodiode). This can be done from the spot to the line just as from the line to the surface. It is simply important that the position and orientation of the recording unit is defined relative to the respective relevant moment in time. By combining two deflector units, provided that their axes of freedom are not linearly dependent on one another, one single spot can be projected onto a surface.

If a reduction of the data detection and evaluation operations is desirable, and if it is sufficient to detect a surface of an object according to only a rough pattern where only striking spots on a surface of an object are measured, then it is possible to use the stereo image method. For this, at least two partial images are produced. By way of example, the deflector device can be provided for at least two rays which are reflected by the object and oriented towards the object at an angle relative to one another, and the recording unit has devices for separately storing and evaluating the, at least two, partial images which are produced from the two separate rays. For the stereo recording method, it is not absolutely necessary to produce a directed optic pay of low divergency and to guide it to the object. Instead, it can be sufficient to illuminate the object sufficiently by general light. In this respect, when we speak of a ray being directed towards the object, this represents only one of any number of rays illuminating the object, namely the ray which leads to the pay which when viewed accordingly is reflected by the object. All these rays which are oriented towards the object (whereby the surface of the object is lightened) then result in a plurality of rays reflected by the object and which result overall in a partial image. To better describe and comprehend the invention it will be assumed that the one partial image is produced by one specific average ray which is in a first angular position relative to the object; and the second partial image is produced by a specific second ray which is at a second angular position relative to the object, wherein the two specific rays are oriented at an angle relative to each other. In other words, the deflector device in the recording optical instrument produces a plan view, so to speak, of the object, whilst, on the other hand an oblique view of the object is produced. Therein, the plan view is merely a special case. The only thing of importance is that two different oblique views are given. In the recording unit both plan views, i.e. both partial images, are recorded. For example, the spots of these partial images are mapped out onto a CCD-surface chip by means of a camera lens, so that electronic data is available separately for each partial image. This data can then be stored and evaluated in such a way that the spatial data can be called up. The partial images which are taken and stored can be put together to give two different complete images for the two different views. These may correspond, for example, to the plan view and the oblique view. The method is known of setting up the height coordinates of the respective points from the various coordinates of the striking spots of the plan view and oblique view which are detected.

Instead of using one single CCD-surface chip, the recording unit can also have two line chips and the carrier can accordingly travel in small steps. Therein, the object or the partial image of it can either be projected by means of one single lens onto two juxtaposed line chips, or by means of two separate lenses with the compulsory use of a ray distributor, onto the two line chips to be arranged in spatially separated manner.

When two separate recording units are used it is possible to arrange the two units at an angle relative to each other in such a way that one single plane mirror in the deflector device is sufficient.

To record image data, CCD cameras (line cameras and surface cameras) and also tube cameras and cameras, can be used which operate with film material, and in the latter case the required evaluation of the partial images taken can be more tedious. Instead of a CCD-line camera it is also possible to use a light-sensitive element to record one single spot, e.g. a photo diode if a mechanical line scanning operation is to be performed, e.g. by means of a rotating or oscillating mirror.

By virtue of the afore-described measuring- and evaluating devices with the apparatus according to the invention for carrying out the stereo-image method it is possible to measure particularly striking features on the surface of an object—in the case of dentistry, for example, to measure the spots on clamping elements for jaw orthopaedics.

Therein, it is particularly advantageous if a screen is arranged between the ray source and the object. By way of example, this can be a screened grid or any other screening surface such as a glass sheet, for example, with a pattern etched thereon. Therefore, a pattern can advantageously be projected onto the surface of the object so that the number of the spots to be measured can be increased in correspondency with the fineness of the grid.

When statically oriented illumination is used, spot patterns, patterned surfaces etc. produce striking spots. The projection of transverse lines (i.e. vertical to the direction of travel) permits a height profile to be plotted along each line, if the angle of the recording ray is different from the angle of projection. This height profile is very useful in measuring the chewing surfaces in dentistry.

The 3D-data is obtained by projecting spots or lines or also patterns onto the surface of an object at a different angle, namely when using a displaced illumination. The projection of spots or lines is a separate operation and in no way has to be done by a deflector optical instrument arranged on the carrier. Likewise, a second carrier is conceivable which carries the deflector optical instrument for projection.

If, for example, a human set of teeth is to be measured for jaw orthopaedic purposes, it is sufficiently firstly to measure some striking spots (the brackets in this case)—for which the stereo image method is suitable—and secondly to obtain quite a rough line screen for the surface (in this case the chewing surfaces of the teeth), for which the light section method is suitable. If a combination of the light section method and stereo-image method is desirable, then it is particularly advantageous if the apparatus according to the invention is characterised in that arranged adjacent to the ray source for the production of an optic ray which extends in one plane: is a recording unit which has a surface camera, and that at a spacing therefrom a deflector device is arranged which is fixed to the carrier, and which is provided for at least two rays which are disposed at an angle relative to each other, which are directed towards the object and which are reflected by the object. With this embodiment, the two partial images first of all have to be produced over the entire length of the object, and in addition data is obtained by travel over the thin line and measuring and evaluation thereof, this line being projected onto the object by the light section method.

Another embodiment of the invention is characterised by a deflector device, fixed to another carrier, which is provided for the purpose of directing the optic ray towards the object, wherein this further carrier is able to travel separately on a further track. There is therefore a first carrier for the ray source and another carrier for the deflector device, and each carrier is able to travel separately on one specific track. It is possible to provide a separate carrier both for the illuminating side and also for the recording side.

Another preferred embodiment of the apparatus according to the invention has a deflector device for directing the optic ray towards the object, wherein this deflector device is fixed to the carrier for the recording deflector unit, and is able to travel jointly therewith. Therefore a separate carrier with drive etc. is provided with this embodiment for each unit. As an alternative, it is possible to direct the optic ray towards the object directly by means of the recording deflector unit, instead of by its own deflector device.

Furthermore, it is expedient according to the invention if a revolving mirror is fixed to the carrier in such a way that the axis of rotation of the revolving mirror is disposed so that it is orthogonal to the direction of movement of the carrier. Therein, care should be taken to ensure that the revolving mirror is characterised by rotary movement. Movement of this kind presupposes a continuous or intermittent rotating movement advancing in one direction, or an oscillating rotating movement in opposite directions. The mirror is obviously responsible for deflecting the optic ray. Therein, the revolving mirror can be fixed to the common carrier for the illuminating side, on the one hand, and for the reflecting side, on the other hand. The revolving mirror is preferably used both to deflect the projected ray and also to deflect the ray used for recording purposes.

The invention is also advantageously designed in such a way that the ray source has devices for the production of an optic ray which extends in a plane, and if the deflector device for directing the linear ray reflected on the object is formed in a recording unit which has a surface camera.

A description has already been given of an embodiment with which the deflector device has at least one plane mirror fixed to the carrier. However, as an alternative, it is particularly expedient, if, according to the invention, the deflector device has two plane mirrors fixed to the carrier at different angles. A deflector device of this kind can be spatially compact, defined by the carrier and moved easily.

As an alternative, with other embodiments, it can also be expedient if according to the invention the direction of the ray of the optic source is fixed at an angle relative to the optical axis of the recording unit, wherein preferably the deflector device has a plane mirror which is fixed to the carrier. If the spatial conditions allow this arrangement to be selected, then the necessary angle is produced between the ray from the optical source and the recording axis of the camera directly and automatically, and both the projection of the ray onto the object and also recording the projected line can be carried out by one and the same plane mirror.

It is also favourable, if, according to the invention, the evaluation unit has devices for forming 3D-data on the basis of the rays which illuminate the object.

With a special instance of application of the measuring apparatus according to the invention for measuring a set of teeth, by using twice the number of active elements within the deflector device it is possible to measure the upper and lower jaws simultaneously. If necessary, the ray sources and recording units must then also be doubled in number.

It is particularly favourable according to the invention to use the apparatus of the embodiments described hereinabove to measure, in contact-free manner, at least one tooth of a set of teeth and/or the position and/or shape of at least one clamping element arranged on the tooth for orthodontal wires, known as brackets. The above-described measuring device according to the invention, on application of the stereo-image method, produces pictures of the object from different viewpoints. By measuring the striking spots in both viewpoints it is possible to determine the spatial coordinates of these spots.

In order to facilitate this measuring operation for the person using the apparatus, e.g. an assistant in a dental laboratory, or even to be able to detect the spots by the use of automated equipment, it is possible to place markings on the clamping elements, known as brackets, with which the wire springs are held, for jaw orthopaedic treatment, and/or go select their shape in such a way that automated detection is possible. These markings may, for example, be imprinted, etched, embedded or provided in relief. To more easily identify the clamping elements (brackets) it is also possible to operate with coloured markings. With one advantageous further embodiment of the invention, it is also provided that an auxiliary measuring element of suitable size and provided with suitable surfaces is inserted into the central groove of the clamping element. By using the clamping elements which usually have a central groove extending in the direction of the row of teeth, the afore-mentioned wire spring is held in place. It is now possible to move the wire spring to a limited extent by hand, and with a high degree of skill on the part of the person using the device. By correctly shaping the wife spring, the desirable forces and moments are applied to the holding elements and thus to the teeth. If it is desirable to compensate for the restricted possibilities of manually bending the wire spring, then it is possible to use wires of different cross-section so that the order of magnitude of the forces is produced by the inherent rigidity of the wire. The cross-section of the central groove (recording axes) in the clamping element thus corresponds to the cross-section of the largest wire which is to be used. Two customary sizes for the height of the groove are 0.47 mm and 0.56 mm and for the depth of the groove, 0.76 mm. The afore-described apparatus according to the invention for optically measuring jaw orthopaedic wire clamping elements permits the use of a computer-controlled bending- or twisting machine to adapt the wire spring to suit the set of teeth of the patient in question. When an apparatus of this kind is used in conjunction with the afore-described optic measurement of the clamping elements, both their position and also the relaxed shape of the wire spring to be used is known. This means that on the basis of the calculation method known in statistics it is possible to make an accurate initial determination or selection of the forces and moments which act upon the clamping elements due to elastic deformation of the wire spring used. In the knowledge of the invention, it is therefore no longer necessary to provide different cross-sections for the wire springs, and so it is no longer necessary to store and handle wire springs of different cross-sections. The square cross-section of 0.41 mm×0.41 mm which is used, amongst others, is sufficient to be able to apply the necessary forces and moments with a wire spring which can be adapted accurately by using the apparatus according to the invention.

It therefore makes sense to use clamping elements wherein the central groove is adapted to suit wires of relatively small cross-section. In the above-mentioned example, this would be a groove of 0.43 mm×0.43 mm. This small groove would reduce the size of the clamping element, the bracket, in particular, becoming flatter which would increase user comfort.

The wire clamping elements used hitherto in jaw orthopaedics are usually not suitable enough for simple or automated optic measuring. In this case, it makes sense to insert the afore-mentioned auxiliary measuring elements into the clamping elements (brackets) for measuring purposes, instead of the wire spring, the shape and design of the auxiliary measuring elements permitting proper identification.

The carrier of the measuring apparatus according to the invention is preferably driven by a step motor or a servo motor, but it can also be drive, in the manner of a film projector, by way of a Maltese cross or a simple pawl mechanism. It is also possible to use a drive in conjunction with a path measuring system so that the current location of the carrier is able to be detected.

If the carrier is driven in step-wise manner, then it is supposed that the smaller the steps from one recording position to the next, the smaller the region of the object to be detected, and thus the smaller the necessary height of the deflector mirror, which can reduce the necessary structural height of the measuring apparatus. This reduction is restricted, since when the deflector mirror is very much reduced in size, the slit diaphragm phenomenon is produced with the result that the necessary illumination intensity increases. The length of the method is preferably adapted to suit possible definition of a light-sensitive surface in the recording unit. When a CDD-camera is used it makes sense to design the steps of the method in such a way that one step on the image plane corresponds to the spacing between lines of the chip, so that only one chip line is evaluated for each mirror view. In practice, the steps of movement for the carrier are expediently in the range of 1/100 to 1 mm. In jaw orthopaedics, a length of 1/10 mm is preferable.

Further features, advantages and possible applications of the present invention will emerge from the following description of preferred embodiments, given in conjunction with the accompanying drawings, wherein:

BRIEF DESCRIPTION OF THE DRAWINGS

FIG. 1 is an illustration of a first embodiment of the measuring apparatus with carrier and with a deflector device fixed thereto, on the one hand, and with a recording unit, on the other hand, FIG. 2 is the same apparatus as in FIG. 1, but illustrating, in addition, the means for plotting a pattern, FIG. 2a is a similar view to FIG. 1, but with other means being provided for plotting a pattern on the surface of the object which are different from those in FIG. 2, FIG. 3 is a similar illustration of the measuring apparatus as in FIG. 1, wherein however, a revolving mirror and ray source with a recording unit for performing the light spot projection method are arranged, FIG. 5 is another embodiment the measuring apparatus with a simplified deflector device ray and directions arranged at angles to one another from the ray source, on the one hand, and towards the recording unit, on the other hand, FIG. 8 is a perspective view of three teeth of a set of teeth with clamping elements (brackets) which are stuck to the outer surface, FIGS. 10 and 10a are further embodiments where the carrier makes revolving movements.

DESCRIPTION OF THE PREFERRED EMBODIMENTS

Figure 4:
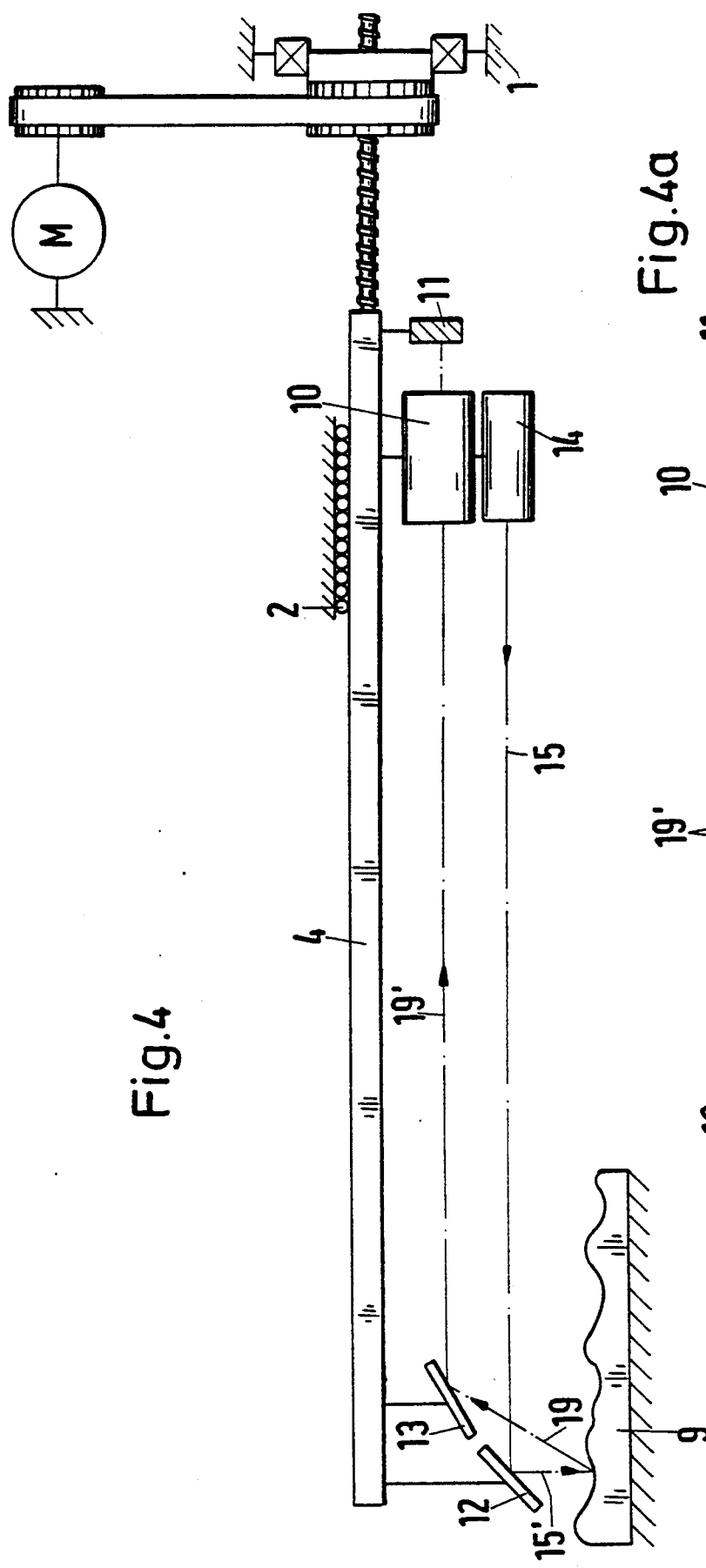
FIG. 4 is an illustration of another embodiment of the measuring apparatus for carrying out the light section method.

The measuring apparatus shown in FIG. 1 is shown only schematically and without the parts of the apparatus which are obvious and known, for the sake of simplifying the description and for the sake of providing a better understanding. Mounted to a frame 1 by way of a ball-bearing 2 is a carrier 4 which travels in a straight line along the two-directional arrow 3, and the carrier is movably mounted to a shaft 5. This latter is driven by a motor 7 (a step motor or a servomotor), also fixed to the frame 1, by means of a toothed belt 6 and a spindle nut, generally denoted by the reference numeral 8, with a belt pulley. The reference numeral 7' is used to denote an integrated measuring system which may be provided for the motor 7.

The object 9 is here illustrated as a surface with three-dimensional extents which is joined to the frame 1, e.g. the object could be the set of teeth in a human mouth. The carrier 4 extends a short spacing away from the object 9 in the direction of the mouth opening, and it is easy to imagine that the carrier can be accommodated inside the mouth cavity with its filaments in the region of the object 9. Disposed in this region are two plane mirrors 12 and 13 which are set at different angles to each other and to the object 9, and at the other end of the elongate carrier 4, thus outside the mouth cavity, the recording device is fixed to the carrier, in the present case this recording device being a camera lens 10 with a CCD-surface chip 11.

As far as these parts are concerned, the embodiments of the measuring apparatus according to FIG. 2 and FIG. 2a are identical in design, and so identical parts are not numbered.

In FIG. 2, a special feature is provided by a ray source 14 which is fixed to the frame 1 and which with the embodiment shown in FIG. 1 and like embodiments is a ray source for the production of a "general brightness", since in the embodiment in FIG. 1 it is sufficient for the surface of the object 9 to be light and for reflected rays to be emitted. On the other hand, with the other embodiments shown, such as in FIG. 2, the ray source 14 is shown separately as one which produces directed rays. In FIG. 2, this ray is shown as a broken line, and is denoted by the reference numeral 15. The actual embodiments described here are concerned with light rays from the visible area. (As an alternative, it is also possible to imagine infra-red- or ultra-violet rays with appropriate transmission- and receiving devices). The ray source 14 contains a lens system, not shown in greater detail, and between this and another lens system 16 is a grid 17 or a grid system which is arranged in such a way that it is projected onto the surface of the object 9 in order to produce striking spots on the surface. This grid 17 can also be a glass panel with etched patterns.

FIG. 2a shows another similar alterative embodiment, wherein the grid 17 is fixed to the frame 1 directly by the surface of the object 9, so that an appropriate optical instrument can be used to throw a shaded pattern onto the surface of the object.

Figure 8A:
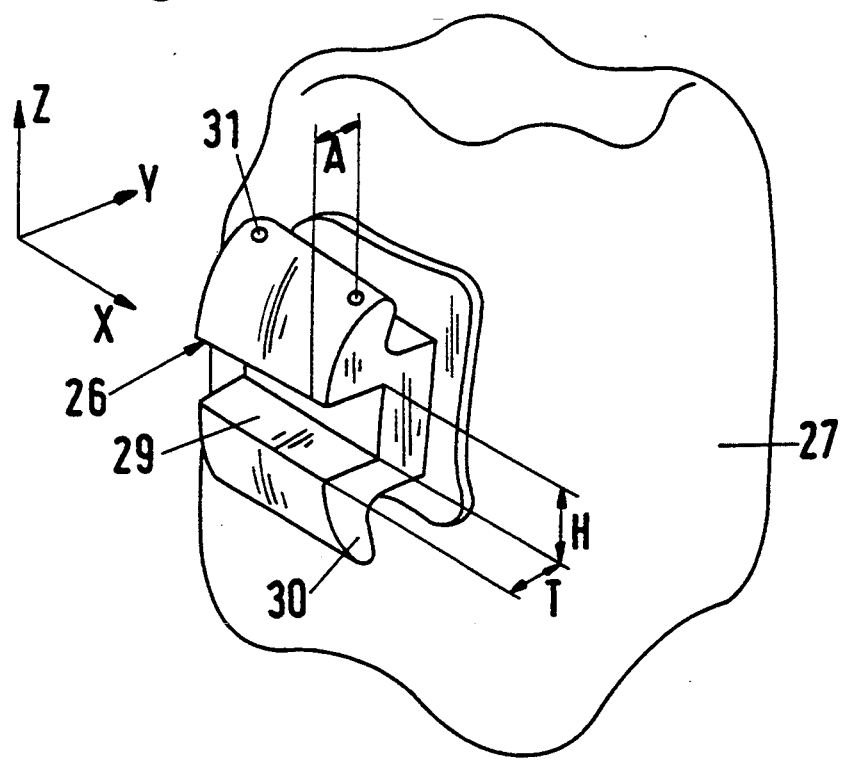
FIG. 8a is a view in perspective of a clamping element on a tooth with the measures shown in perspective.

As in FIG. 8a, the arrow 3 is to be imagined as passing along an X-axis. An imaginary Y-axis extends vertically to the X-axis and vertically to the drawing plane.

When the surface of the object 9 is illuminated appropriately, reflected rays are produced and are guided to the recording unit 10, 11. By way of example, the reflected ray 18 extends (in the plan view) vertically to a main surface disposed in an X-Y-plane onto the outer plane mirror 12 where it is deflected and is guided in the form of a reflected ray 18' into the lens 10 and is suitably mapped on the surface chip 11. This produces a first partial image. Another reflected ray 19 is representative of the other reflected rays for producing another partial image, this other reflected ray being oriented towards the plane mirror 13 and there being guided, after deflection, in the form of a ray 19' to the camera lens 10. The ray 18' forms a plane view in the recording unit 10, 11, and the other mirror 13 produces an oblique view by the reflected ray 19'. By electronically processing the output signal Of the chip 11, not described here in greater detail, it is possible to store and evaluate the two partial images separately. In addition, the aforedescribed drive of the carrier 4 makes it possible to know the exact location of the carrier and thus that of the deflector device 12, 13 relative to the object 9. The partial images which are recorded and stored are put together to form two complete images which correspond to the images of the plan view and of the oblique view. As already stated hereinabove, the different coordinates of the striking spots in both views make it possible to calculate the height coordinates. The carrier 4 is preferably displaced in small steps of 1/10 mm along the two-directional arrow 3, from the back to the front, for example, i.e. in the drawings from the left to the right for the purpose of measuring from a starting position (left) to the end position (right) where the reflected rays 18 and 19 emanate from the outermost edge of the object 9 shown in the drawings. The evaluation unit is denoted by the reference numeral 11a and is connected to the chip 11. It is only shown in FIG. 1, but is also to be imagined as existing in the other embodiments.

The stereo-image method is described by way of FIGS. 1 to 2a.

The light spot projection method will now be described with the aid of FIG. 3.

Disposed at the rear, outer end of the carrier 4 are the two mirrors 12 and 13, and further to the right and drivable with the carrier 4 are the light source 14 on the fixing rod which is denoted by the reference numeral 20 and also the camera lens 10 with the CCD-line-chip 11 arranged behind it.

In addition, a revolving mirror 22 is fixed to the carrier 4 so that it can travel therewith by way of a second step motor or servomotor 21, in such a way that the axis 23 of the revolving mirror 22 is vertical to the translatory movement, in a straight line, along the two-directional arrow 3. The ray which is directed from the ray source 14 and which is of low divergency and small diameter 15 is deflected on the revolving mirror 22 and impinges the outer plane mirror 12 as a ray 15', this plane mirror throwing the ray onto the surface of the object 9, whence it is guided towards the other plane mirror 13 in the form of a reflected ray 19, like in FIG. 1, and is thence deflected and is guided as a ray 19' onto the revolving mirror 22 where it is deflected and is guided into the lens 10.

The rays are deflected by the revolving mirror 22 by virtue of the plurality of mirror surfaces shown. When it moves the ray is pivotable in oscillating manner in at least one plane in such a way that the light ray 15', after being deflected by the plane mirror 12, passes over the entire width of the object 9 to be measured. The reflected ray 19' is also recorded by the revolving mirror 22. Thereby, use of a vertical CCD-line-chip 11 is sufficient onto which the camera lens 10 projects the light spot. The current angular position of the revolving mirror 22 and thus also the data relating to the line position currently being scanned is accurately known.

The revolving mirror 22 shown in FIG. 3 thus performs two functions: firstly, the ray 15 produced in the ray source 14 (here the light source) is deflected laterally (pivotable in oscillating manner), and secondly the ray 19, 19' reflected by the object 9 is deflected by the same mirror surface of the revolving mirror 22, back into the camera lens 10, so that from the viewpoint of the camera the lateral deflection of the ray 15' projected onto the object cannot be seen. For this reason, for computational processing, the lateral deflection (measured by the instantaneous angle of rotation of the mirror 22), must be known. As an alternative, however, the projected light spot can be recorded by a camera which is oriented directly onto the plane mirror 13. Here, however, a surface camera would have to be used since both the lateral deflection of the ray which is caused by the revolving mirror 22 and also the deflection in height which appears in the plane mirror 13 must be recorded.

The lateral deflection of the ray which is visible directly in the camera (chip camera 11) abandons the need to measure the instantaneous angle of rotation of the revolving mirror 22.

FIG. 5 shows another embodiment of the measuring apparatus for the light section method. Other recording methods can be described with the aid of this drawing. For example, it is not necessary to produce the necessary angles for the measuring method between the light ray 15 and the optical axis (which in FIG. 5 coincides with the reflected ray 19' or is disposed so that it is, at least, parallel thereto) of the camera 10 by two plane mirrors arranged at different angles from the mirrors 12 and 13 in the previous drawings. Instead, it is also possible to arrange the ray source 14 so that it is clearly higher or lower than the camera 10, so that the necessary angle is produced at the outset or automatically due to this arrangement. In this case, one single deflector mirror 12' can suffice (instead of two separate deflector plane mirrors 12 and 13).

Figure 4A:
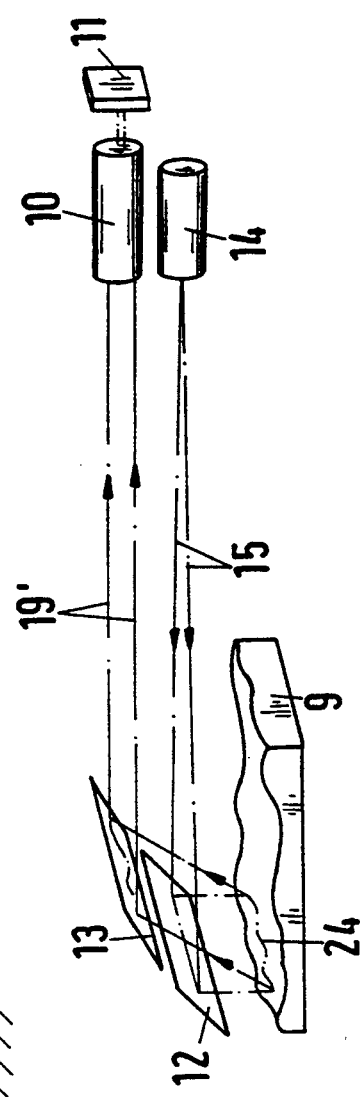
FIG. 4a is the same apparatus as that in FIG. 4, but in the main showing the main parts in a perspective view (omitting the carrier)

The light section method will be described with the aid of FIGS. 4 and 4a. The view in perspective in FIG. 4a shows the spread out ray 15 which is emanated from the ray source 14, and above it the reflected ray 19' which is guided into the camera 10. The ray source 14 produces a light ray as with the above-described light spot projection method. However, this ray extends in the plane shown at the bottom of FIG. 4a, so that a thin line 24 is projected by the rear plane mirror 12 onto the object 9 which is recorded by the camera 10, 11 by way of the other plane mirror 13 as a reflected ray plane 19'. Here, it is necessary to use a surface camera for the thin line 24 which is projected onto the object only appears in the plan view of the ray 15' which impinges from above vertically as a straight line, and in the direction of the reflected rays is an oscillating line.

The light source 14 can also be arranged at another angle to the camera lens 10, wherein the ray 15 is then directed, via deflector mirrors and/or ray distributors, not shown, at the necessary angle onto the rear outer plane mirror 12.

To return once again to FIG. 5, the light section method can also be used when only one single plane mirror 12' is used as the deflector device. If spatial conditions permit such an arrangement to be used as that shown in FIG. 5, then the necessary angle is directly produced between the ray source 14 and the recording axis (parallel to the ray 19') of the camera 10, 11. The light ray 15, 15' can then be projected onto the object 9, by way of the same plane mirror 12' as used to record the projected line 19'.

The combination of the light section method and stereo-image method will be described with the aid of FIG. 6.

The advantage with the light section method of being able to measure all spots of a surface (as opposed to the stereo-method where only striking spots can be measured) is put to one side by the requirement of a large amount of data which is produced during recording, for one surface image must be recorded for each line to be scanned, thus with a step-wise drive for each step of the carrier 4. With the stereo-image method it is sufficient to record one line only.

Figure 6:
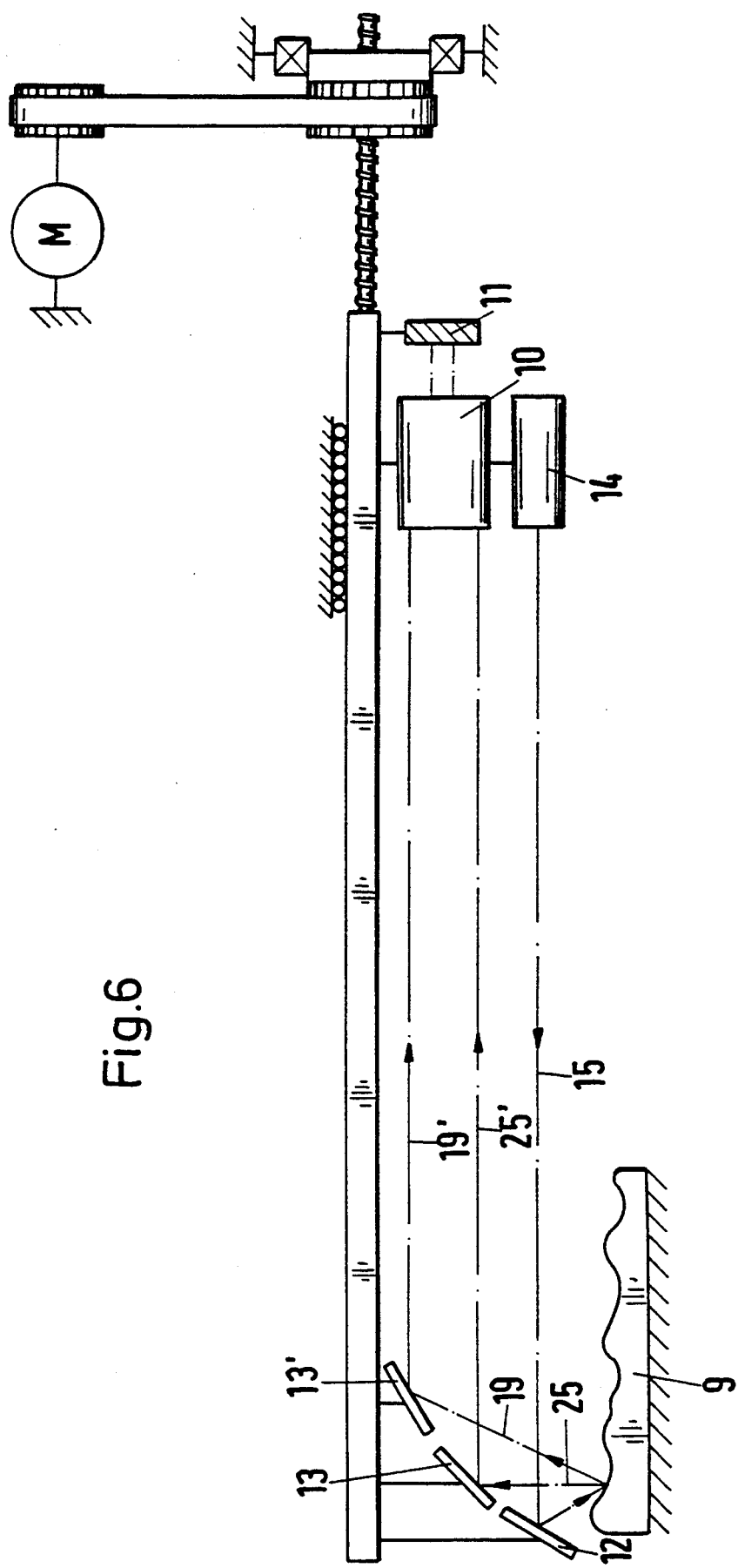
FIG. 6 is a similar illustration as in the preceding drawings, but of another embodiment with the combined stereo image and light section method.

With the embodiment in FIG. 6, the apparatus is basically the same as that in FIG. 1. In FIG. 6, a ray source 14 which produces a directed ray is simply provided, which, like the embodiment in FIG. 4, produces an expanded light ray 15. The outer plane mirror 12 projects the light ray 15 back onto the surface of the object 9. In addition, the light section method is combined with the stereo-image method so that reflected rays 19, 19' are also recorded by way of the front-most inner plane mirror 13' by the recording unit 10, 11, or alternatively rays 25 reflected by the surface of the object, and are recorded after being reflected on the central deflector plane mirror 13. The plane mirror 13 and 13' thus records rays 25', to which end two plane mirrors are needed.

As with the embodiment in FIG. 5, if spatial conditions so permit, it is also possible to arrange the ray source 14 at an angle, shown in FIG. 5, relative to the optical axis of the camera, so that the plane mirror 12 can then be abandoned.

With the straightforward stereo-image method, if the optical axis of one or both lenses is arranged at an angle to the direction of the ray source it is also possible to manage with one plane mirror 13 or 13' alone.

Figure 7:
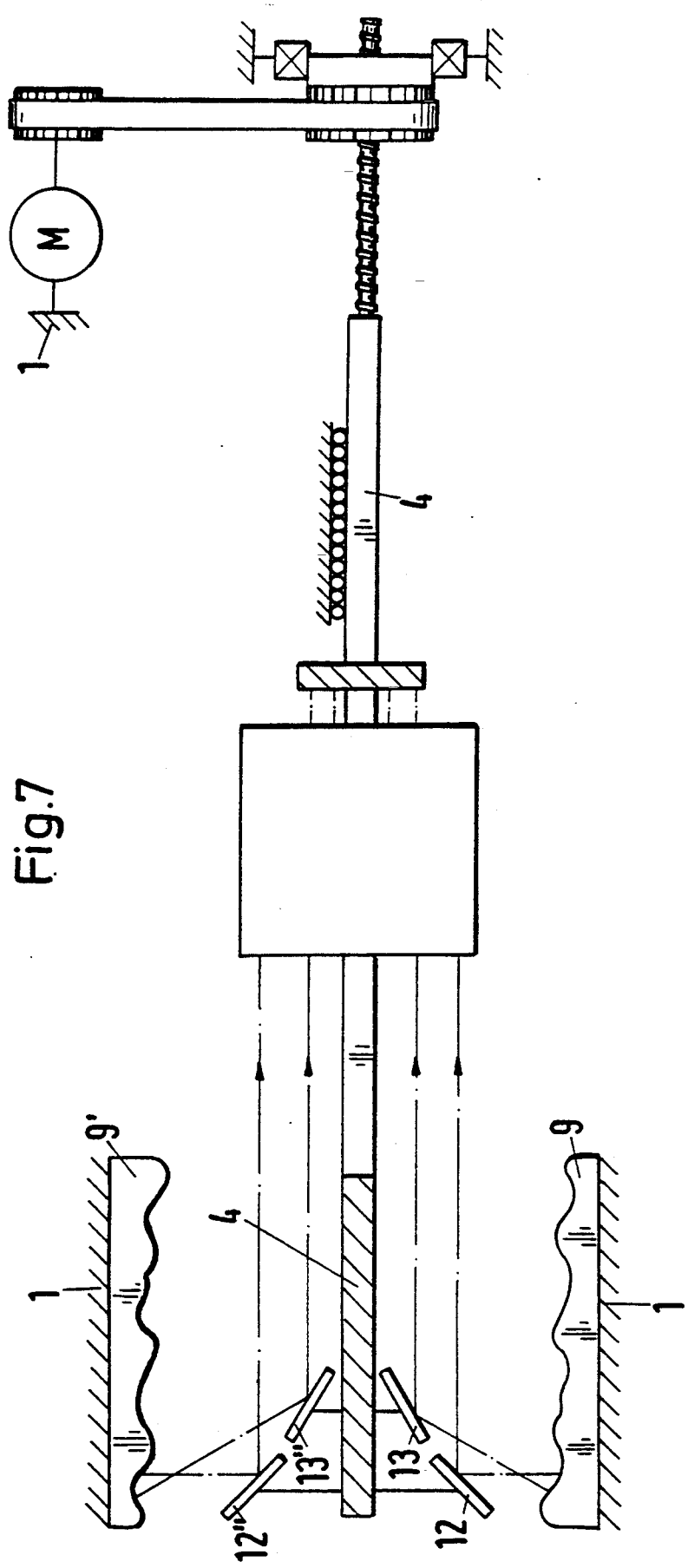
FIG. 7 is another embodiment of the measuring apparatus with twice the measuring range.

FIG. 7 shows a similar apparatus as that in FIG. 1, wherein however the dimensions have simply been doubled. This embodiment is used for simultaneously measuring the upper and lower jaws of a mouth 9, 9'. Usually, in dentistry, this is rigidly coupled with the frame 1 by way of a glass panel, e.g. by touching or clamping, for the teeth are fixed to the jaw and not to the base plate 1 illustrated here beneath the object 9 and beneath the object 9'.

Here, four plane mirrors 12, 13, 12", 13" are used in mirror-symmetrical relationship to the central plane, this plane extending through the common carrier 4. In this way, it is possible to measure the upper and lower jaws simultaneously.

With respect to the particular use of the measuring apparatus according to one of the afore-described embodiments, a description will be given with the aid of FIGS. 8 to 9a of the possibility of designing the wire clamping element 26 and auxiliary measuring elements 33 and 33' for jaw orthopaedics.

The afore-described measuring apparatus can be used to improve the optical detection of the afore-mentioned clamping elements 26 (so-called brackets).

FIG. 8 shows the set of teeth consisting of three teeth 27, wherein a clamping element 26 is arranged by way of clamping surfaces 28 on the outer surface of the tooth 27.

Figure 8B:
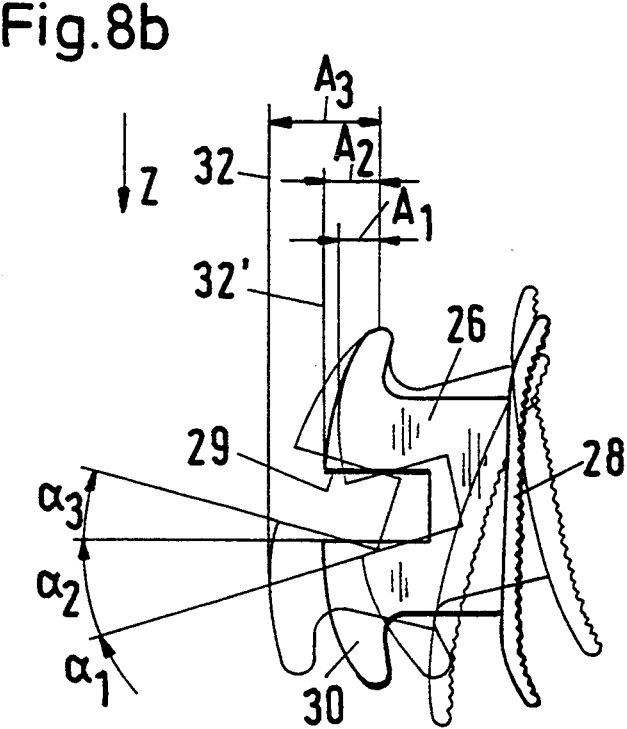
FIG. 8b is a view of the clamping element in the direction of the set of teeth, with dimensions given.

The clamping element is of mushroom-shaped cross-section (in the Z-Y-plane in FIG. 8a) in FIG. 8b, wherein passing through the longitudinal extent (X-extent) of the clamping element 26 is a central groove 29. This latter is used to receive the wire spring 41. Hook-like limbs 30 are attached on either side to the central groove 29, about which limbs a rubber ring 31, to the left in FIG. 8, is fixed, or wrapped, to fix the wire spring 41 to the clamping element 26.

The geometry is described with the aid of FIG. 8a. Arranged on the outer ends of the hook-like limbs 30 are two marking spots on the surface of the clamping element 26, possibly by way of pressing, inserting, boring or soldering. These markings 31 are raised sufficiently optically from the rest of the surface of the clamping element 26 to permit the striking spot 31 to be detected and measured accurately and by automated means.

If the spatial coordinates of these spots are known, the X-, Y- and Z-coordinates of the clamping element 26 and also its angular position about the Y- and Z-axis are known. The spacing of these spots 31 from the edge of the clamping element which appears as a line in the projection of the Z-extent and which is marked by the boundary line 32 in FIG. 8b (or 32' for another size), the angular position about the X-axis is produced, shown in FIG. 8b by the angle α 1 or α2 or α3. In order to permit more accurate measuring of this angular position, it is possible to select the contour of the outer surface of the clamping element 26, thus the surface remote from the tooth 27, in such a way that inside a given anatomically sensible angular region for each horizontal spacing A1 or A2 or A3 measured (FIG. 8b) an accurately set angular position is produced from the outer surface of the clamping element, the line according to the projection 32 or 32' etc., to the marking spots.

In FIG. 8a it is also possible to see the customary heights H of the central groove 29 of 0.47 mm and 0.56 mm (for the dimension H) and the depth T of the central groove 29 of 0.76 mm, for example.

Figure 9:
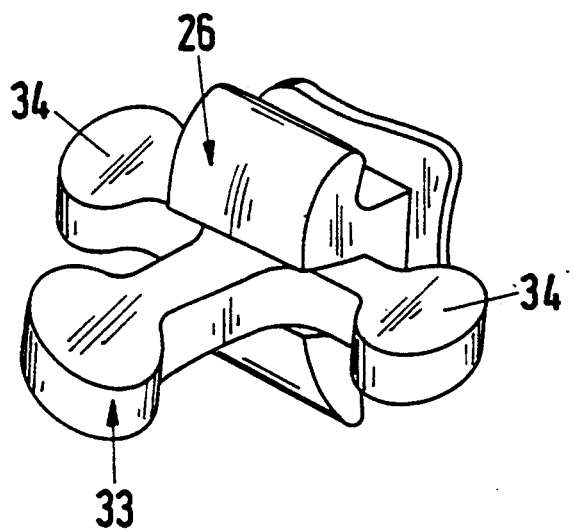
FIG. 9 is a view in perspective of a clamping element with an inserted auxiliary measuring element.
Figure 9A:
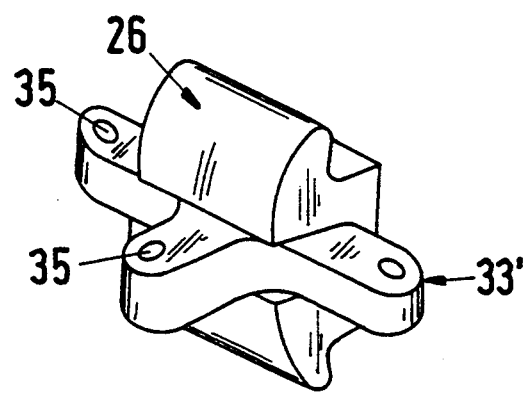
FIG. 9a is a view in perspective of a clamping element of a different shape and with an auxiliary measuring element inserted therein.

Two different embodiments of auxiliary measuring elements 33 and 33' can be seen in FIGS. 9 and 9a.

In FIG. 9, the auxiliary measuring element 33 is of a T-shaped configuration in the plan view, and has rounded regions of increased thickness 34 at the ends of the limbs. The thickness of the auxiliary measuring element is equal to the height of the central groove 29 and is formed by two parallel planes which are disposed at appropriate spacings apart. Thereby, the auxiliary measuring elements are plate-shaped in the X-Y-plane and they have a flat, smooth surface.

With the auxiliary measuring element 33' in FIG. 9a, the ends of the limbs are designed without the aforementioned regions of increased thickness provided with the embodiment according to FIG. 9, and are thus of a T-shaped configuration in the Z-extent plan view of the auxiliary measuring element 33'.

Both the partially circular rounded configuration of the auxiliary measuring element 33' in plan view and also the embodiment 34 of increased thickness with the auxiliary measuring element according to FIG. 9 defines an outer contour which allows three central spots to be measured. On the basis of the spatial coordinates of these three central spots it is then possible to accurately define the position of the clamping element 26. As an alternative, instead of arranging the central spots it is also possible to provide markings 35 on the ends of the limbs, as shown in the case of the auxiliary measuring element 33' in FIG. 9a.

FIG. 10 shows another embodiment for application of the apparatus for the light section method. Reference can also be made to FIG. 4.

The carrier 4 is mounted in the frame 1 about the point of rotation 42. Accordingly, it performs a rotating movement along the arrow 3 pointing in different directions. The drive here is in the form of a toothed segment 37 which is fixedly connected to the carrier 4. The pinion 38 of a geared motor 39 engages in this toothed segment 37. The geared motor 39 is preferably designed as a step motor with step-down gearing, but it can also be in the form of a servomotor with a step-down gearing. The motor 39 is also fixed to the frame 1.

The deflector device performs a movement through an arc about the point of rotation 42, so that under the geometric conditions shown the spacing relative to the object 9 is changed. This is not a problem if only a small region is to be measured (marked on the object 9 with the two-directional arrow at the bottom to the left), in the case of a single tooth, for example. The necessary angle of pivotal movement of the carrier 4 would only be small, and the change to the spacing of the deflector device relative to the surface of the object would be correspondingly small.

Since, on the basis of the known geometric conditions, the movement of the deflector device 12, 13 in this extent is known, it can easily be compensated for computationally when the image data is evaluated.

Figure 10A:
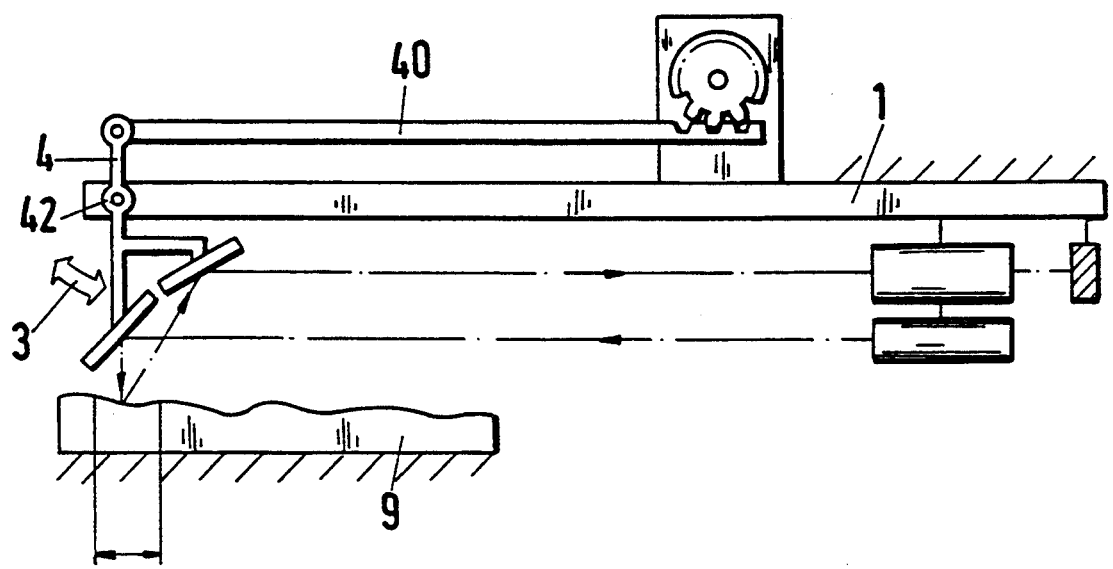

FIG. 10a shows another embodiment, wherein the deflector device also performs a rotating movement. By virtue of the frame 1, here in the form of a fixed elongate rod, the point of rotation 42 is guided very close to the deflector unit. The carrier 4 is simply a small, short lever which carries the deflector device. The drive is by way of a connecting rod 43 which is driven, like in FIG. 10, by a geared motor.

We claim:

1. An apparatus for optical measurement of a poorly accessible, three-dimensional object comprising:
   a) frame means for connection to the object to prevent relative movement of the frame means and the object;
   b) carrier means movably mounted on the frame means;
   c) actuator means for moving the carrier means to a plurality of positions relative to the frame means;
   d) position determining means for determining the position of the carrier means relative to the frame means;
   e) optical ray source means for directing at least one optical ray towards at least a portion of the object;
   f) deflector means disposed on the carrier means for deflecting at least one reflected optical ray from at least a portion of the object towards a recording unit, and adapted to move with the carrier means to a plurality of positions to provide a plurality of reflected optical rays to the recording unit; and
   g) means for evaluating the plurality of reflected optical rays received by the recording unit comprising means for storing image data corresponding to the reflected optical rays and means for processing the stored image data.

2. An apparatus according to claim 1, wherein the carrier means comprises a linear carriage that is mounted on a straight, linear guide track that is mounted on the frame means.

3. An apparatus according to claim 1, wherein the carrier means is pivotally mounted on the frame means.

4. An apparatus according to one of claims 1 to 3, wherein the apparatus comprises at least one further deflector means for oscillatingly deflecting the reflected optical rays and for projecting the reflected optical rays into the recording unit.

5. An apparatus according to claim 4, wherein the at least one further deflector means comprises a revolving mirror rotatably mounted to the carrier means and having an axis of rotation orthogonal to the direction of movement of the carrier means.

6. An apparatus according to claim 1, wherein the deflector means comprises means for deflecting at least two optical rays that are reflected from the object at an angle with respect to each other, and the evaluating means comprises means for forming three-dimensional data from the at least two optical rays.

7. An apparatus according to claim 1, wherein the evaluating means is movably adjustable with respect to the frame means.

8. An apparatus according to claim 1, wherein the optical ray source means comprises means for providing data to the evaluating means.

9. An apparatus according to claim 8, wherein the apparatus comprises further deflector means for deflecting the at least one optical ray in at least one plane.

10. An apparatus according to claim 8, wherein a grid is disposed between the optical ray source means and the object.

11. An apparatus according to claim 8, wherein the deflector means comprises means for aligning the at least one optical ray relative to the object.

12. An apparatus according to claim 8, wherein the deflector means is fixed to the carrier means and moves together with the carrier means.

13. An apparatus according to claim 8, wherein the deflector means comprises a revolving mirror rotatably mounted to the carrier means and having an axis of rotation orthogonal to the direction of movement of the carrier means.

14. An apparatus according to claim 8, wherein the optical ray source means comprises means for producing a planar optical ray, and the deflector means comprises means for orienting a linear optical ray reflected from the object into the recording unit, wherein the recording unit comprises a surface camera.

15. An apparatus according to claim 8, wherein the evaluating means comprises means for the generation of three-dimensional data from the plurality of reflected optical rays.

16. An apparatus according to claim 1, wherein the deflector means comprises at least one plane mirror fixed to the carrier.

17. An apparatus according to claim 16, wherein the at least one optical ray of the optical ray source is at an angle relative to an optical axis of the recording unit.

18. An apparatus according to claim 1, wherein the deflector means comprises two plane mirrors fixed to the carrier at different angles.

19. An apparatus according to claim 1, wherein the object comprises at least one tooth having a clamping element provided thereon.

20. An apparatus according to claim 19, wherein at least one marking is provided on a surface of the clamping element.

21. An apparatus according to claim 19, wherein a central groove is provided in the clamping element and an auxiliary measuring element is inserted into the central groove.

* * * * *

UNITED STATES PATENT AND TRADEMARK OFFICE
CERTIFICATE OF CORRECTION

PATENT NO. : 5,424,836
DATED : June 13, 1995
INVENTOR(S) : Weise et al.

It is certified that error appears in the above-indentified patent and that said Letters Patent is hereby corrected as shown below:

Column 2, line 21, "t°" should read --to--.

Column 7, line 45, "pay" should read --ray--.

Column 9, line 7, please omit colon ":".

Column 10, line 41, "gc" should read --to--.

Column 10, line 56, "wife" should read --wire--.

Column 13, line 57, "plane" should read --plan--.

Column 13, line 60, "Of" should read --of--.

Signed and Sealed this

Tenth Day of October, 1995

Attest:

BRUCE LEHMAN

Attesting Officer

Commissioner of Patents and Trademarks